United States Patent [19]

Szentmiklósi et al.

[11] Patent Number: 5,244,880
[45] Date of Patent: Sep. 14, 1993

[54] STABLE AQUEOUS SOLUTIONS OF PRYMICIN AND PHARMACEUTICAL AND COSMETIC COMPOSITIONS CONTAINING THESE SOLUTIONS

[75] Inventors: Péter Szentmiklósi; Tamás Szüts; György Hidasi; István Juhász, all of Budapest, Hungary

[73] Assignee: Chinoin Gyogyszer- ES Vegyeszeti Termekek Gyara, Budapast, Hungary

[21] Appl. No.: 835,097

[22] Filed: Feb. 11, 1992

Related U.S. Application Data

[63] Continuation of Ser. No. 430,505, Nov. 1, 1989, abandoned.

[30] Foreign Application Priority Data

Nov. 2, 1988 [HU] Hungary ................................ 5669/88

[51] Int. Cl.⁵ ............................................... A61K 31/70
[52] U.S. Cl. ...................................... 514/31; 514/788; 514/970; 514/844; 536/6.5
[58] Field of Search ............................ 514/23; 519/31; 536/6.5

[56] References Cited

U.S. PATENT DOCUMENTS

| | | |
|---|---|---|
| 3,920,814 | 11/1975 | Bocher et al. ................ 424/227 |
| 4,064,238 | 12/1977 | Bocher et al. ................ 424/115 |
| 4,782,141 | 11/1988 | Dekany et al. ................ 536/6.5 |
| 4,789,667 | 12/1988 | Makino et al. ................ 514/161 |
| 5,064,815 | 11/1991 | Szentmiklosi et al. ......... 514/31 |

OTHER PUBLICATIONS

Szentmiklosi et al, Chemical Abstract vol. 108 (1988) No. 62454h.

Primary Examiner—Johnnie R. Brown
Assistant Examiner—Elli Peselev
Attorney, Agent, or Firm—Herbert Dubno; Jonathan Myers

[57] ABSTRACT

The invention relates to novel stable aqueous primycin solutions containing 0.5 to 1.75% by mass/volume of primycin sulfate or 2.5 to 9% by mass/volume of a complex of primycin N-methylpyrrolidone and 2 to 15% by mass/volume of pyroglutamic acid, preferably L-pyroglutamic acid or a soluble salt, preferably the sodium salt thereof as calculated for the volume of the solution to be prepared and 40 to 60% by volume of isopropanol as calculated for the volume of the solution to be prepared as well as water in an amount adding up to 100%. The stable, aqueous primycin solutions are topical antibiotics.

3 Claims, No Drawings

STABLE AQUEOUS SOLUTIONS OF PRYMICIN AND PHARMACEUTICAL AND COSMETIC COMPOSITIONS CONTAINING THESE SOLUTIONS

This is a continuation of co-pending application Ser. No. 07/430,505 filed on Nov. 1, 1989, now abandoned.

FIELD OF THE INVENTION

The invention relates to a stable aqueous solution of primycin which is useful to a topical therapeutic treatment in itself or in liquid or semisolid compositions. The invention further relates to the preparation of the aqueous solution and the compositions.

BACKGROUND OF THE INVENTION

The antibiotic known as "primycin" has first been described in the Hungarian patent specification No. 153,539; it was extracted as a native antibiotic from the product of a fermentation carried out with the culture of Thermopolyspora galeriensis fungal strain. Primycin mainly acts on gram-positive cocci, is not absorbable and is useful for a topical treatment. The preparation of primycin has been published in J. Chem. Soc. Perkin I 1984, 816 wherein primycin was characterized by a single formula. However, it is now known that this substance is a mixture consisting of several components (cf. the Hungarian patent specifications Nos. 195,514 and 196,425). Although primycin is a very effective antibiotic, its therapeutical utilization was made extraordinarily difficult since it is practically insoluble either in water or in physiologically acceptable solvents. Thus, several efforts had earlier been made to eliminate these difficulties and to prepare pharmaceutical compositions containing primycin in a therapeutically well utilizable form while maintaining its efficiency as a whole.

Thus, the preparation of a semisolid composition containing primycin as a heterocolloid in 50% aqueous ethanol was suggested in the Hungarian patent specification No. 173,708. However, by using this process, a gel containing at most 0.2% of primycin can be prepared with the further disadvantage that a burning pain sensation on the damaged skin surface is elicited. This problem is avoided by adding a local anesthetic agent to the composition whereby an allergic response can be evoked in the patient. A further disadvantage consists in that skin damage can occur by a long-lasting treatment with such a composition as it has been proved by animal experiments carried out on New Zealand rabbits.

A composition containing the complex of primycin sulfate with N-methyl-pyrrolidone in a predetermined weight ratio and suggested in the Hungarian patent specification No. 194,493 proved to be preferred. This composition having a gel consistency is useful to incorporate the active ingredient in a micro-distribution practically in all galenic forms such as ointments, creams, foams, dusting powders and the like, however, it is not useful to prepare transparent solutions.

There exists, however, an area of dermatology which demands an antibiotic treatment, i.e. the skin disease caused by Propionibacterium acne, the various types of which are usually treated by painting with alcoholic solutions of antibiotics namely, both the patient and the disease require the cleaning and drying effects of alcohol. Since this treatment does not involve any durable exposition (as opposed to the semisolid heterocolloid containing alcohol), this painting with an alcoholic solution can be used without any danger.

For alcoholic paintings, antibiotics with a tetracycline—skeleton as well as erythromycins had been used for a long time; however, most pathogens became resistant to these antibiotics. Due to its very high price, the use of clindamycin, introduced in recent years, has not become wide-spread.

The aqueous alcohol-based compositions of this kind known up to the present usually contain about 50% of alcohol and 1 to 1.5% by mass of antibiotic dissolved therein such as Staticin 1.5 topical solution (Physicians' Desk Reference 40, Ed. Medical E. Comp. USA 1986).

Primycin which destroys in a concentration as low as $10^{-7}$ g/ml both the Propionibacterium acne as well as Staphylococcus bacteria, being present as co-pathogens, would be considered to be an ideal antibiotic for the topical therapy of acne if a solution of at least 1% concentration could be prepared from it. However, such a solution could not until now be prepared from primycin since primycin sulfate dissolves up to 0.2% as a maximum in ethanol or propanol. This problem is solved by the process according to the present invention which overcomes any difficulty in obtaining a solution containing primycin in a concentration of even 1.5% by mass.

SUMMARY OF THE INVENTION

In the course of these investigations, it has suprisingly been recognized that, on mixing a salt or another suitable derivative of primycin with an appropriate amount of pyroglutamic acid in isopropanol under heating, a milky suspension in obtained which is transformed to a limpid, stable solution after dilution with water while continuously stirring under heating. The solution thus obtained remains limpid and stable after cooling down and can be used by itself for therapeutic treatments, mainly for topical treatments; but it is useful also for the preparation of topically used common pharmaceutical compositions such as gels, foams, aerosols and the like by using known methods of formulation and pharmaceutically acceptable additives.

This recognition is novel and highly surprising since the process can be accomplished by using only the adequate weight ratios of the substance mentioned and specifically by using the substances mentioned above. Thus, isopropanol can not be replaced by other alcohols or solvents since no suspension, convertible to an aqueous solution can be obtained by using e.g. methanol, ethanol, butanol, octanol or polyvalent alcohols such as ethylene glycol or glycerol; and similarly, pyroglutamic acid cannot be replaced by other amino acids, e.g. glutamine, asparagine, alanine or glycine. Similarly, no satisfactory results are obtained when other amounts, e.g. an other concentration of isopropanol are used which are different from the preferred weight ratios to be described hereinafter.

Namely, it has been found that a clear, stable solution can be obtained only in the case when 0.5 to 1.75% by mass volume of primycin sulfate and 2 to 15% by mass/volume of pyroglutamic acid (optionally in the form of one of its soluble salts, preferably the sodium salt) as calculated for the volume of the solution to be prepared, are suspended while stirring and heating suitably at a temperature of 40° to 60° C. to obtain a solution containing 40 to 60% by volume of isopropanol after dilution with water.

Thus, the present invention relates to novel, stable aqueous primycin solutions containing 0.5 to 1.75% by mass/volume of primycin sulfate and 2 to 15% by mass/volume of pyroglutamic acid, preferably L-pyroglutamic acid or a soluble salt, preferably the sodium salt thereof as calculated for the volume of the solution to be prepared and 40 to 60% by volume of isopropanol as calculated for the volume of the solution to be prepared as well as water in an amount adding up to 100%.

The invention further relates to a process for the preparation of the above novel stable aqueous solutions, which comprises suspending 0.5 to 1.75% by mass/volume of primycin sulfate and 2 to 15% by mass/volume of pyroglutamic acid, preferably L-pyroglutamic acid or a soluble salt, preferably the sodium salt thereof, as calculated for the volume of the solution to be prepared while stirring and heating suitably at a temperature of 40° to 60° C., diluting the milky suspension thus obtained for the desired concentration with water while stirring, then cooling down and, if desired, transforming the solution thus obtained to a topically applicable pharmaceutical or disinfecting cosmetic composition by adding the usual pharmaceutical or cosmetical auxiliary materials and optionally other therapeutically active, suitably desquamating and/or antiinflammatory agent(s).

According to a preferred embodiment of the invention, primycin is used as a complex formed with N-methylpyrrolidone mentioned above instead of its sulfate to obtain stable solutions with very advantageous properties. Preferably, a complex containing 20% by weight of primycin is used in an amount of 2.5 to 9% by mass/volume for the preparation of the stable aqueous solution according to the invention.

The clear, stable solutions according to the invention can be formulated to topically applicable pharmaceutical compositions by using known techniques. Disinfecting cosmetic compositions such as ointments, creams, foams and aerosols or animal food concentrates (for veterinary medicinal use) can similarly be prepared by using the above solutions. In the course of preparing these compositions, a therapeutically useful preparation containing the primycin salt or the complex formed from primycin with N-methyl-pyrrolidone can also be used: e.g. the EBRIMYCIN NMP$^R$ gel (Chinoin, Budapest) based on the Hungarian patent specification No. 194,493 mentioned hereinabove is useful for this purpose.

In the composition according to the invention, pyroglutamic acid can also be used in the form of a preparation optionally containing therapeutically and/or cosmetically preferable additives. Pyroglutamic acid may e.g. conveniently be used in the form of LACTIL$^R$, a composition of Th. Goldschmidt AG. (German Federal Republic) containing cosmetically or dermatologically preferred additives such as collagen and carbohydrates in addition to 25% by mass of sodium pyroglutamate (see, "Lexikon der Hilfstoffe" Vol. II, Ed. Cantor, Aulendorf, page 511, 1981).

The invention is illustrated in detail by the following non limiting Examples.

EXAMPLE 1

1.0 g of primycin sulfate and 8.0 g of 1-pyroglutamic acid are suspended in 50 ml of isopropanol at 50° C. in a water bath while vigorous stirring, then the milky suspension is filled up to 100 ml with distilled water at the same temperature under vigorous stirring and allowed to cool down to room temperature to obtain a limpid, stable solution.

EXAMPLE 2

5.0 g of a complex of primycin with N-methyl-pyrrolidone (containing 1.0 g of primycin) and 8.0 g of L-pyroglutamic acid are transformed to a suspension with 50 ml of isopropanol at 50° C. in a water bath while vigorously stirring, then the milky suspension thus obtained is filled up to 100 ml with distilled water under vigorous stirring and cooled down to room temperature to obtain a limpid, stable solution.

EXAMPLE 3

The process described in Example 1 is followed, except that 10.0 ml of LACTYL$^R$ (containing 2.5 g of pyroglutamic acid) are used instead of 8.0 g of L-pyroglutamic acid. A limpid, stable solution is obtained.

EXAMPLE 4

The process described in Example 1 is followed by using 7.5 g of the complex of primycin with N-methyl-pyrrolidone (containing 1.5 g of primycin) and 10.0 ml of LACTYL$^R$ (containing 2.5 g of pyroglutamic acid) as starting substances to give a limpid, stable solution.

EXAMPLE 5

The process described in Example 1 is followed by using 1.5 g of primycin sulfate and 9.0 g of sodium L-pyroglutamate as starting substances to obtain a limpid, stable solution.

EXAMPLE 6

After suspending 1 g of primycin sulfate and 14 g of DL-pyroglutamic acid in 45 ml of isopropanol at 50° C. in a water bath under vigorous stirring, the milky suspension thus obtained is filled up to 100 ml with distilled water at the same temperature while stirring vigorously to give a limpid, stable solution.

EXAMPLE 7 Preparation of an aerosol

After melting 5.0 of EBRIMYCIN NMP$^R$ gel (containing 1.0 g of primycin) together with 8.0 g of L-pyroglutamic acid at 60° C. while stirring, 52.0 g of isopropanol are gradually added, then the mixture is filled up to 100 ml with distilled water and maintained at 60° C. under constant stirring until a clear solution is obtained.

10 parts by mass of Frigen 11/12 expelling gas are pressed to 90 parts by mass of the above solution cooled to room temperature in an aerosol bottle by using a suitable filling system.

Instead of the Frigen expelling gas, the aerosol can be prepared also with a propane-butane expelling gas by using an appropriate equipment.

EXAMPLE 8 Preparation of a foam

For the preparation of an emulsion which may be used as a foam, the solutions are prepared in two phases (phases "A" and "B", respectively), which are composed as follows.

| | | |
|---|---|---|
| Phase "A": | EBRIMYCIN NMP ® gel (containing 20% by mass of prymicin) | 3.75 g |
| | LACTIL ® (containing 25% by mass of pyroglutamic acid) | 7.50 g |
| | Isopropanol | 7.50 g |
| | Distilled water | 26.00 g |
| Phase "B": | Paraffin oil | 5.00 g |

| | |
|---|---|
| Isopropyl myristate | 5.00 g |
| EMULGEATOR E 2149 ® (Goldschmidt, German Federal Republic) | 5.00 g |
| Stearin | 10.25 g |

EMULGATOR E 2149 ® is a trademark of an emulsifier which is a mixture of polyoxyethylene (7) stearyl ether and stearyl alcohol. It is non-ionic and self-emulsifying, and is a waxy, solid mass.

Both phase are separatively homogenized at 60° C., then phase "A" is poured in a thin stream to phase "B" and the mixture obtained is stirred until it is cooled down. The emulsion thus prepared is filled into a foam-spraying bottle together with the expelling gas.

EXAMPLE 9 Preparation of a gel

A gel is prepared from the solution according to the invention by using the following components.

| | |
|---|---|
| EBRIMYCIN NMP ® gel | 4.50 g |
| Lactil | 9.00 g |
| Isopropanol | 45.00 g |
| Distilled water | 31.50 g |
| Carbopol 940 | 2.00 g |
| Triethanolamine | 2.00 g |
| Tagat L (Goldschmidt) | 4.00 g |
| Tagat M (Goldschmidt) | 2.00 g |

As described above, EBRIMYCIN NMP$^R$ gel is stirred with LACTIL$^R$ and the solvents at 60° C., then Carbopol 940 composition is mixed to. After clearing up of the solution, the mixture of Tagat L, Tagat M and triethanolamine previously melted together is flown to the solution in a thin stream under constant stirring, then the mixture obtained is further stirred until it achieves a gel consistency.

EXAMPLE 10

Preparation of a combined solution with an antibacterial and antiinflammatory action.

The solution is prepared from the following components:

| | |
|---|---|
| Primycin sulfate | 1.00 g |
| L-Pyroglutamic acid | 9.00 g |
| Hydrocortisone acetate | 1.00 g |
| Oxolinic acid | 1.00 g |
| Isopropanol | 64.00 g |

Filled with distilled water up to 100 ml.

Hydrocortisone acetate, oxolinic acid and the primycin salt are mixed together and pulverized to fine granules. The gel is prepared by dissolving this powder mixture in N-methylpyrrolidone at 65° C. and then cooling down to room temperature. After heating the gel thus formed again to 60° C., L-pyroglutamic acid is mixed to, the mixture obtained is emulsified in isopropanol at the same temperature and then stirred after adding distilled water as hot until a clear solution is obtained.

EXAMPLE 11 Preparation of an animal food concentrate for therapeutic use

The solution prepared according to Example 1 is applied onto a carrier which is useful for consumption by animals such as corn-grits, wheat-grits, bentonite, aerosil, talc or calcium carbonate in a fluidizing apparatus or in any other apparatus which may be used for atomization, then dried at a temperature of 20° to 40° C. preferably under reduced pressure. In the course of this process, the active ingredient content of the animal food concentrate is adjusted to between 0.1 and 0.5%.

We claim:
1. A stable, aqueous primycin solution, for administration as a topical antibacterial which consists essentially of 0.5 to 1.75% by weight or volume primycin sulfate or 2.5 to 9% by weight or volume of a complex of primycin with N-methyl-pyrrolidone and 2 to 15% by weight or volume of pyroglutamic acid or a soluble salt thereof as calculated for the volume of the solution to be prepared and 40 to 60% by volume of isopropanol as calculated for the volume of the solution to be prepared as well as water in an amount adding up to 100%.

2. A primycin solution as defined in claim 1, wherein the pyroglutamic acid is L-pyroglutamic acid.

3. A pharmaceutical or disinfecting cosmetic composition, which consists essentially of a primycin solution as defined in claim 1 in admixture with a pharmaceutically acceptable inert carrier.

* * * * *